US00PP26682P3

(12) United States Plant Patent
Giumarra et al.

(10) Patent No.: US PP26,682 P3
(45) Date of Patent: May 3, 2016

(54) GRAPEVINE PLANT NAMED 'ARRATWENTYSEVEN'

(50) Latin Name: *Vitis vinifera*
Varietal Denomination: ARRATWENTYSEVEN

(71) Applicant: AGRICULTURAL RESEARCH AND DEVELOPMENT LIMITED LIABILITY COMPANY, Bakersfield, CA (US)

(72) Inventors: Sal Giumarra, Bakersfield, CA (US); Shachar Karniel, Bakersfield, CA (US)

(73) Assignee: Agricultural Research and Development Limited Liability Company, Bakersfield, CA (US)

( * ) Notice: Subject to any disclaimer, the term of this patent is extended or adjusted under 35 U.S.C. 154(b) by 289 days.

(21) Appl. No.: 13/998,057

(22) Filed: Sep. 26, 2013

(65) Prior Publication Data

US 2015/0089695 P1 Mar. 26, 2015

(51) Int. Cl.
*A01H 5/08* (2006.01)

(52) U.S. Cl.
USPC ..... Plt./205
CPC ..... *A01H 5/0812* (2013.01)

(58) Field of Classification Search
USPC ..... Plt./205
CPC ..... A01H 5/0812; A01H 5/08
See application file for complete search history.

(56) References Cited

PUBLICATIONS http://fccjxxw.com/m/4a733b4a5ef7ba0df480c0d3.html; 2010, 2011; 11 pages.*

* cited by examiner

*Primary Examiner* — Kent L Bell
(74) *Attorney, Agent, or Firm* — Lewis Roca Rothgerber Christie LLP

(57) ABSTRACT

A new distinct variety of grapevine named ARRATWENTYSEVEN abundantly forms attractive large crisp, meaty & juicy berries with a small seed trace and with a blue/black skin coloration; in large clusters which display a naturally sweet flavor. The fruit commonly is ready for harvesting during August in San Joaquin Valley of Central California, U.S.A, and displays good eating qualities as a table grape. The fruit firmness renders the fruit well amenable for handling, shipping, and storage.

1 Drawing Sheet

Classification: The present invention relates to a new *Vitis vinifera* Grapevine.

Variety denomination: The new Grapevine has the varietal denomination 'ARRATWENTYSEVEN'.

BACKGROUND OF THE INVENTION

A breeding program was initiated during the late 90's near Bakersfield in the San Joaquin Valley of Central California. In 2004, during this breeding program, a new variety of *Vitis vinifera* was created by deliberate cross breeding of two parent plants by emasculation of the pollen bearing organ of the female and introducing pollen from another male origin. The female parent of the new variety was the A.R. which is a black medium size seedless grape variety (non-patented in the United States). The male parent (i.e. the pollen parent) of the new variety was GAW 6 which is a large black fleshy table grape variety with a very small seed trace and medium fertility (non-patented in the United States).

Comparison of ARRATWENTYSEVEN with its parents:

| | ARRATWENTYSEVEN | A.R. (Mother) | GAW 6 (Father) | Autumn Royal (Comparison Variety) |
|---|---|---|---|---|
| Seed trace | Small | None | Small | Prominent seed trace |
| Berry shape | Narrow ellipsoid | Ovoid | Round | Ovoid |
| Bunches per vine | 42 | 32 | 32-36 | 30-35 |
| Fertility | High | Medium | Medium to high | Medium |

The parentage of the new variety can be summarized as follows:

A.R.AGAW 6

An artificial pollination was created, and the result was an embryo which possessed unique genetic qualities. The rudiments resulting from the above pollination were embryo rescued.

In 2005 the plant was transplanted to Bakersfield in San Joaquin Valley of Central California.

It was found that the new grapevine of the present invention possesses the following combination of the characteristics:

(a) Forms attractive large crisp, meaty & juicy berries with a small seed trace and with a blue/black skin coloration; in large clusters which display a naturally sweet flavor,
(b) Commonly bears fruit during the month of August in the San Joaquin Valley of Central California, U.S.A., and
(c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2007 near Bakersfield in the San Joaquin Valley of Central California, U.S.A. by grafting on mature Thompson rootstock (non-patented in the United States). Such asexual propagation has been conducted thereafter in successive years through 2008, and has shown that the characteristics of the new variety are strictly transmissible from one generation to another. Accordingly, the new variety undergoes asexual propagation in a true to type manner.

SUMMARY OF THE INVENTION

The new variety ARRATWENTYSEVEN is a medium size, blue/black table grape with a small seed trace and with a very high production, e.g., about 42 bunches per vine, and an average of about one to two bunches per shoot.

Asexual reproduction by micro propagation of the new variety as performed near Bakersfield, Calif., U.S.A., shows that the forgoing and other distinguishing characteristics come true to form and are established and transmitted through succeeding propagations.

BRIEF DESCRIPTION OF THE DRAWING

The accompanying photographic illustration shows typical specimens of vegetative growth of six year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRATWENTYSEVEN'

DETAILED BOTANICAL DESCRIPTION

The chart used in the identification of colors is The R.H.S. Colour Chart of The ROYAL HORTICULTURAL SOCIETY published in 1995. The description is based on the observation of plants growing on 'Thompson Seedless' rootstock outdoors near San Joaquin Valley of Central California, U.S.A.

Vine:
- *Vigor.*—Vigorous upright shoots.
- *Productive capacity.*—Bearing at a natural, average capacity. Spur pruning.
- *Trunk.*—Strong and developed. Diameter: Ranges from 2"-2⅜. Height above ground at which diameter was observed: 36". Rough with a fibrous, shaggy exterior. Color: Light maple brown (177-B).

Time of bud burst: Early. Date of bud burst in specified location of culture is Feb. 26, 2013 in Bakersfield, Calif.

Young shoot:
- *Openness of tip.*—Slightly open.
- *Prostrate hairs on tip.*—Medium.
- *Anthocyanin coloration of prostate hairs on tip.*—Medium.
- *Erect hairs on tip.*—Medium.

Young leaf:
- *Color of upper side of blade.*—Light copper red.
- *Prostrate hairs between main veins on lower side of blade.*—Sparse.
- *Erect hairs on main veins on lower side of blade.*—Sparse.

Shoot:
- *Attitude (before tying).*—Semi-erect.
- *Color of dorsal side of internodes.*—Green and red yellow green (144-A; stripped grey red 148-B).
- *Color of ventral side of internodes.*—Green (yellow green 144-A).
- *Color of dorsal side of nodes.*—Green and red (yellow green 144-A; stripped greyed red 178-B).
- *Color of ventral side of nodes.*—Green (yellow green 144-A).
- *Erect hairs on internode.*—Sparse.
- *Length of tendrils.*—Medium (1 inch).
- *Color of tendrils.*—Yellow Green (146-D).

Flower:
- *Sexual organs.*—Fully developed stamens and fully developed gynoecium.

Mature leaf:
- *Size of blade.*—Medium (7.5×8 inches).
- *Shape of blade.*—Circular.
- *Blistering upper side of blade.*—Medium.
- *Number of lobes.*—Seven.
- *Depth of upper lateral sinuses.*—Shallow.
- *Arrangement of lobes of upper lateral sinuses.*—Slightly overlapped.
- *Arrangement of lobes petiole sinus.*—Half open.
- *Length of teeth.*—Medium.
- *Ratio length/width of teeth.*—Medium.
- *Shape of teeth.*—Both sides convex.
- *Typically observed leaf apex.*—Acute.
- *Proportion of main veins on upper side of blade with anthocyanin coloration.*—Absent in mature leaves.
- *Prostrate hairs between main veins on lower side of blade.*—Sparse.
- *Erect hairs on main veins on lower side of blade.*—Sparse.
- *Length of petiole compared to length of middle vein.*—Moderately lower.
- *Top side color.*—Green (137-B).
- *Bottom side color.*—Yellow Green (146 B).
- *Texture.*—A little rough.
- *Vein color.*—Yellow Green (146-C).
- *Petiole length.*—5".
- *Petiole diameter.*—3/16".
- *Petiole color.*—Yellow Green (146-D).

Reproductive organs:
- *Stamen color.*—Green (137-C).
- *Stamen size.*—0.003125".

Time of beginning of ripening: Jul. 25, 2013 Bakersfield, Calif. season.

Bunch:

*Size* (*peduncle excluded*).—Medium 8×7 inches.

*Density*.—Dense.

*Length of peduncle primary bunch*.—2¼".

*Diameter of peduncle primary bunch*.—5/16".

*Average bunch weight*.—1.5 lbs.

Berry:

*Size*.—Medium.

*Length*.—12/16".

*Shape*.—Narrow ellipsoid.

*Diameter*.—1-1¼ inch.

*Weight*.—10-12 grams.

*Color of skin* (*without bloom*).—Blue black 202-A.

*Ease of detachment from pedicel*.—Difficult.

*Pedicel length*.—7/16".

*Pedicel diameter*.—⅛".

*Pedicel color*.—Dark green 146-B.

*Thickness of skin*.—Medium.

*Anthocyanin coloration of flesh*.—Light green 145-D with anthocyanin coloration.

*Firmness of flesh*.—Moderately firm.

*Particular flavor*.—None.

*Formation of seeds*.—Small rudiment.

*Market use observed plant*.—Fresh market.

*Berries per bunch*.—110-150 berries.

Woody shoot:

*Main color*.—Orange brown (grayed orange 165-C).

Tendrils:

*Number*.—5 at bloom.

*Color*.—Yellow Green (146-D).

Age and growing conditions: Six years growing under Y system in South Joaquin Valley (hot, dry summers).

Shipping characteristics:

(*E.g. number of days fruit has been stored under specific conditions*).—Fruit was in cold storage. Stored in poly bags inside Styrofoam boxes with sulphur pads.

*After* 60 *days*.—Rachises were 60% green; 3% berry shuttering; no be wrinkling or cracks were apparent.

DNA profile: To further the characterize the new Arra variety DNA was extracted from dried leaf samples and DNA profiles were obtained in California, USA using base pairs for 10 standard microsatellite DNA markers. The data is presented hereafter.

| Microsatellite DNA Marker | Allele Sizes in Base Pairs | |
|---|---|---|
| M 1 | 240 | 240 |
| M 2 | 239 | 253 |
| M 3 | 181 | 181 |
| M 4 | 210 | 212 |
| M 5 | 251 | 259 |
| M 6 | 151 | 155 |
| M 7 | 187 | 189 |
| M 8 | 247 | 257 |
| M 9 | 194 | 212 |
| M 10 | 241 | 247 |

The ARRATWENTYSEVEN variety has not been observed under all possible environmental conditions to date. Accordingly, it is possible that the phenotypic expression may vary somewhat with changes in light intensity and duration, cultural practices, and other environmental conditions.

What is claimed is:

1. A new and distinct variety of grapevine plant, botanically known as *Vitis vinifera* identified as 'ARRATWENTYSEVEN', substantially as shown and described herein.

* * * * *

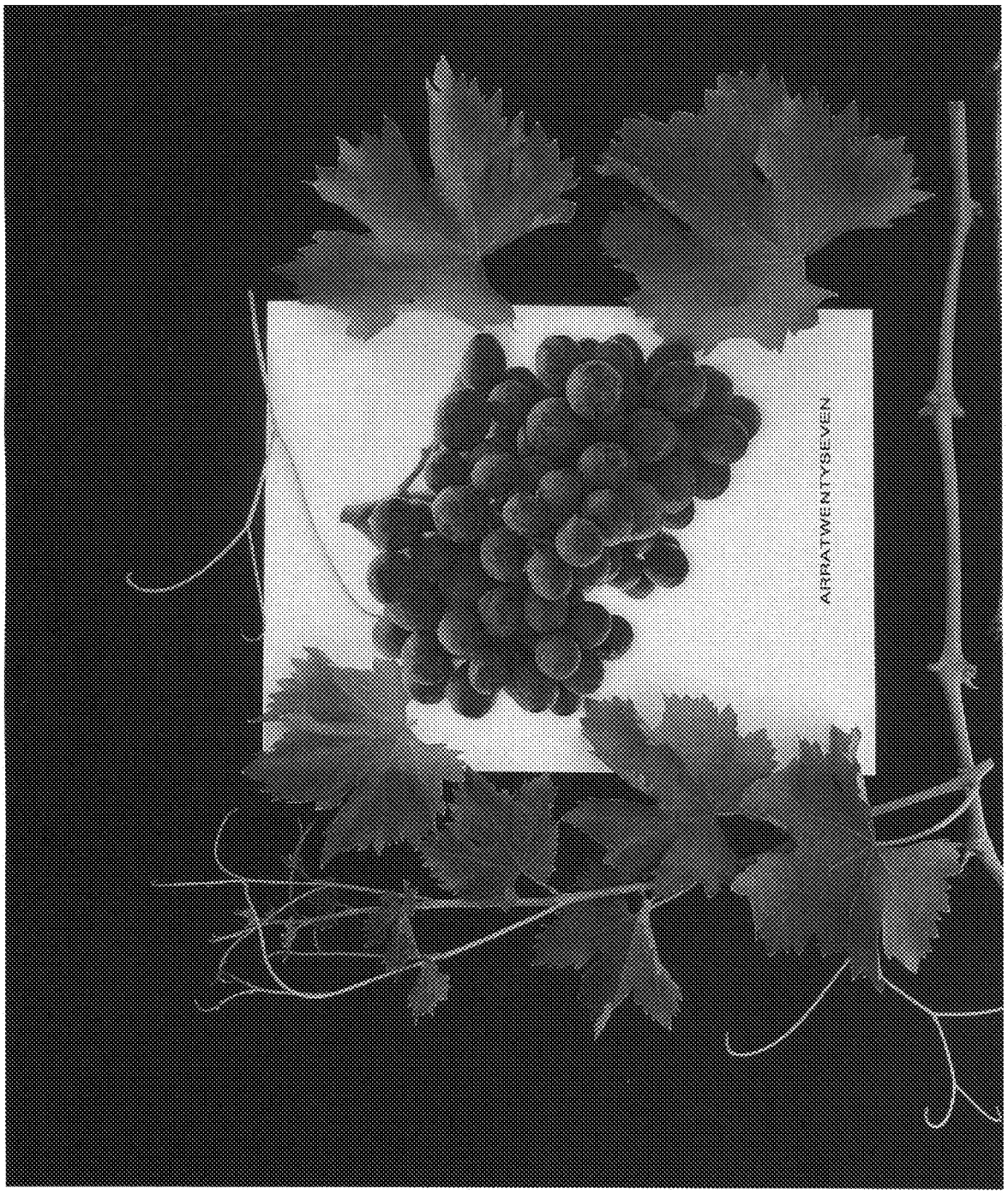
ARRATWENTYSEVEN